United States Patent
Samain et al.

(10) Patent No.: US 6,346,230 B1
(45) Date of Patent: *Feb. 12, 2002

(54) AEROSOL DEVICE BASED ON ALCOHOLIC COMPOSITIONS OF FIXING MATERIALS

(75) Inventors: Henri Samain, Bievres; Patrick Minou, Courbevoie, both of (FR)

(73) Assignee: L' Oreal, S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/985,213

(22) Filed: Dec. 4, 1997

(30) Foreign Application Priority Data

Dec. 4, 1996 (FR) ............................................. 9614329

(51) Int. Cl.[7] ................................................. A61L 9/04
(52) U.S. Cl. ........................................ 424/45; 424/70.1
(58) Field of Search ....................... 424/45, 47, DIG. 1, 424/DIG. 2, 70.11

(56) References Cited

U.S. PATENT DOCUMENTS

| | | | |
|---|---|---|---|
| 4,192,862 A | * 3/1980 | Pengilly ........................ | 424/47 |
| 4,397,836 A | * 8/1983 | Madrange et al. ............. | 424/47 |
| 4,650,094 A | * 3/1987 | Werding ........................ | 222/55 |
| 5,021,238 A | * 6/1991 | Martino et al. ......... | 424/DIG. 2 |
| 5,094,838 A | * 3/1992 | Benson et al. .......... | 424/DIG. 1 |
| 5,125,546 A | * 6/1992 | Dunne et al. ................ | 222/394 |
| 5,126,126 A | * 6/1992 | Varaprath et al. .............. | 424/47 |
| 5,148,952 A | * 9/1992 | Candat ................... | 222/402.22 |
| 5,176,898 A | * 1/1993 | Goldberg et al. .............. | 424/47 |
| 5,266,303 A | 11/1993 | Myers et al. | |
| 5,304,368 A | * 4/1994 | Shernov et al. ................ | 424/47 |
| 5,614,173 A | * 3/1997 | Ulmer et al. .................. | 424/47 |

FOREIGN PATENT DOCUMENTS

| | | |
|---|---|---|
| WO | 95/00105 | 1/1995 |
| WO | 95/03776 | 2/1995 |
| WO | 95/33437 | 12/1995 |
| WO | 96/32918 | 10/1996 |

OTHER PUBLICATIONS

Martino, G. T et al. (1992). Spray Technology & Marketing, Mar. Issue, pp. 34–39.*
Johnsen, M. A. (1992). Spray Technology & Marketing, Jun. Issue, pp. 32–40.*

* cited by examiner

Primary Examiner—Thurman K. Page
Assistant Examiner—Robert M. Joynes
(74) Attorney, Agent, or Firm—Finnegan, Henderson, Farabow, Garrett & Dunner, L.L.P.

(57) ABSTRACT

An aerosol device comprising a container containing an aerosol composition including a liquid phase containing at least one fixing material in a suitable solvent and a propellant and a means for distributing the aerosol composition, where the fixing material has a glass transition temperature (Tg) of greater than or equal to 30° C., and the aerosol device is suitable for obtaining a solids flow rate for the aerosol composition ranging from approximately 4 to approximately 17 mg/s and a wetting power for the aerosol composition of greater than or equal to 50 mg/s, and a process for treating keratin fibers using the aerosol device.

18 Claims, No Drawings

AEROSOL DEVICE BASED ON ALCOHOLIC COMPOSITIONS OF FIXING MATERIALS

The present invention relates to novel aerosol devices intended for fixing the hair.

The hair products for shaping and/or holding the hair style which are most widely available on the cosmetics market are spray compositions essentially consisting of a solution, usually an alcoholic or aqueous solution, and one or more materials, generally polymer resins, whose function is to form welds between the hairs, these materials also being known as fixing materials, as a mixture with various cosmetic adjuvants. This solution is generally packaged either in a suitable aerosol container placed under pressure with the aid of a propellant, or in a pump-dispenser bottle.

The fixing materials are generally fixing polymers, that is to say film-forming polymers that are soluble in water and in alcohol, such as polyvinylpyrrolidone, the vinylpyrrolidone/vinyl acetate copolymers described in particular in U.S. Pat. Nos. 3,929,735 and 3,770,683, vinyl acetate/crotonic acid copolymers and anionic or amphoteric acrylic resins. These materials make it possible to obtain the fixing effect easily but, on the other hand, after brushing or combing, hair under the usual lacquer conditions looks stiff and feels coarse, or even sticky.

These drawbacks are associated with several parameters, among which mention may be made of the nature of the fixing polymer(s), or alternatively the nature of the welds. In order to overcome these drawbacks, it is thus possible to alter these two parameters without, however, decreasing the desired fixing effect. In order to improve the cosmetic properties of the fixing materials, it has been proposed to combine different polymers, for example as discussed in documents WO 94/12148, WO 96/06592 and U.S. Pat. No. 5,158,762.

The inventors have now found, surprisingly, that by appropriately selecting the fixing polymers and the diffusion parameters for the compositions, it is possible to decrease the size of the welds.

The present invention thus relates to a novel aerosol device intended to fix the hair, which makes it possible to decrease the size of the welds and thus to provide excellent cosmetic properties such as softness, disentangling and feel while at the same time retaining good fixing and/or shaping qualities for the hair style.

The aerosol device according to the invention comprises a container containing an aerosol composition including, on the one hand, a liquid phase (or fluid) containing at least one fixing material in a suitable solvent and, on the other hand, a propellant, and a means for distributing the aerosol composition, the fixing material having a glass transition temperature (Tg) of greater than or equal to 30° C., and the device being suitable for obtaining a solids flow rate ranging from approximately 4 to approximately 17 mg/s and a wetting power greater than or equal to 50 mg/s.

The distribution means generally includes a distribution valve controlled by a distribution head, which itself comprises a nozzle through which the aerosol composition is vaporized.

The terms "Tg", "solids flow rate" and "wetting power" as understood according to the present invention are defined below.

According to the present invention, the term glass transition temperature (Tg) is understood to refer to the Tg of the fixing material in the dry extract, the dry extract consisting of all of the non-volatile materials in the fluid, or solids.

According to the present invention, the solids flow rate ($F_S$) corresponds to the amount of dry extract which leaves the aerosol device per unit time. This solids flow rate is expressed in mg/s and is calculated by multiplying the solids concentration in the aerosol composition ($C_S$) by the flow rate of the aerosol composition at the nozzle outlet ($F_{AC}$):

$$F_S = C_S \times F_{AC}$$

The solids concentration in the aerosol composition ($C_S$) corresponds to the amount of solids relative to 100 g of aerosol composition (fluid+propellant). The solids concentration is expressed as a percentage and is measured after spraying by evaporation of the volatile components of the spray residue for 1 hour 30 at 105° C.

The flow rate of aerosol composition ($F_{AC}$) corresponds to the amount of aerosol composition (fluid+propellant) leaving the aerosol device per unit time. It is expressed in mg/s and is measured by the difference between the weight of aerosol before ($M_0$) and after ($M_1$) spraying for 10 seconds:

$$F_{AC} = (M_0 - M_1)/10.$$

According to the present invention, the wetting power corresponds to the amount of product received on a sheet of plastic placed 35 cm away from the nozzle of the aerosol device for a given unit of time. In this case, the product comprises the solids plus some of the solvent which has not evaporated in the course of the trajectory plus, optionally, some of the propellant which has not evaporated. This wetting power is expressed in mg/s and is measured, according to the invention, by the following method:

a sheet of plastic 21 cm×23 cm in size is suspended vertically from a precision balance (1/1000), the sheet being connected to the balance via the upper edge (generally by a balance hook inserted into a perforation placed at the center of the width and 1 cm from the upper edge), and held vertically by applying a weight centered on the lower edge (generally by means of a clamp fixed and centered on the lower edge);

a block is placed behind the lower edge of the sheet in order to keep the sheet vertical during impact of the product;

the aerosol device is placed vertically such that the composition diffusion nozzle is positioned at the center of and 35 cm away from the vertical sheet, for vaporization of the product perpendicular to the sheet;

the composition is vaporized for 5 seconds the amount of product received on the vertical sheet is measured as soon as the vaporization has ended.

For greater precision, it is possible to use a suitable device comprising a means for supporting the aerosol device and means allowing the three-dimensional control of the position of the nozzle relative to the vertical sheet. This device can also be equipped with a pneumatic device for controlling the spray (firing and duration), so as to control the duration of the vaporization precisely. The whole assembly can be controlled by computer.

In order to avoid environmental disturbances, the trajectory of the product between the nozzle and the sheet will advantageously be protected horizontally and vertically by the walls of a tunnel of appropriate dimensions.

Lastly, vaporization of the product is advantageously carried out under a controlled atmosphere, preferably at a temperature of 20° C. and a relative humidity of 50%.

According to a preferred embodiment of the invention, the aerosol device according to the invention is suitable for obtaining a solids flow rate of less than 16 mg/s, preferably ranging from 6 to 15 mg/s.

Advantageously, the aerosol device according to the invention is suitable for obtaining a wetting power ranging from 50 mg/s to 125 mg/s.

The solids flow rate and wetting power characteristics of the aerosol devices according to the invention depend, on the one hand, on the aerosol composition, and, on the other hand, on the means of distribution, the two needing to be suitable in order to obtain the desired characteristics. Among the parameters liable to influence these characteristics, mention will be made more particularly of the solids concentration ($C_S$), the flow rate of aerosol composition ($F_{AC}$) and the phase of the aerosol composition.

Advantageously, the solids concentration ($C_S$) ranges from 0.4 to 5% by weight relative to the total weight of the aerosol composition (fluid+propellant), preferably from 0.6 to 3.25% by weight.

The flow rate of aerosol composition ($F_{AC}$) will, in this case, be suitable for obtaining a solids flow rate ($F_S$) as defined above. Preferably, the $F_S$ will range from 500 to 700 mg/s, more preferably in the region of 550 mg/s.

The phase of the aerosol composition is preferably a long phase, that is to say that the fluid/propellant weight ratio is greater than 1, more preferably ranging from 1.2 to 3.

The fixing material comprises at least one fixing polymer, alone or in combination with common cosmetic additives, for example plasticizers, or neutralizing agents.

According to the invention, any fixing polymer known per se can be used. A fixing polymer selected from anionic, cationic, amphoteric and nonionic polymers and mixtures thereof can be used in particular. The fixing polymers can be used in solubilized form or in the form of dispersions of solid polymer particles.

The cationic fixing polymers which can be used according to the present invention are preferably selected from polymers containing primary, secondary, tertiary and/or quaternary amine groups forming part of the polymer chain or connected directly thereto, and having a molecular weight preferably ranging from about 500 to about 5,000,000 and more preferably from 1000 to 3,000,000.

According to the present invention, the fixing polymers are preferably anionic or amphoteric polymers.

The anionic fixing polymers generally used are polymers containing groups derived from carboxylic acid, sulphonic acid or phosphoric acid and have a weight-average molecular weight ranging from approximately 500 to approximately 5,000,000. The carboxylic groups are provided by unsaturated mono- or dicarboxylic acids monomers such as those corresponding to the formula (II):

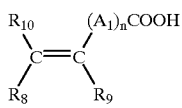

(II)

in which:
n is an integer from 0 to 10,
$A_1$ denotes a methylene group, optionally connected to the carbon atom of the unsaturated group, or to the neighboring methylene group when n is greater than 1, via a hetero atom such as oxygen or sulphur,
$R_{10}$ denotes a hydrogen atom or a phenyl or benzyl group,
$R_8$ denotes a hydrogen atom or a lower alkyl or carboxyl group, and
$R_9$ denotes a hydrogen atom, a lower alkyl group or a —$CH_2$—COOH, phenyl or benzyl group.

In the abovementioned formula, a lower alkyl radical preferably denotes a group having 1 to 4 carbon atoms and in particular methyl and ethyl.

The anionic fixing polymers containing carboxylic groups which are preferred according to the invention are:

A) Homo- or copolymers of acrylic or methacrylic acid or salts thereof and in particular the products sold under the names VERSICOL E or K by the company Allied Colloid and ULTRAHOLD by the company BASF. The copolymers of acrylic acid and of acrylamide sold in the form of their sodium salt under the names RETEN 421, 423 or 425 by the company Hercules, the sodium salts of polyhydroxycarboxylic acids.

B) Copolymers of acrylic or methacrylic acids with a monoethylenic monomer such as ethylene, styrene, vinyl esters, acrylic acid esters or methacrylic acid esters. These copolymers can be grafted onto a polyalkylene glycol such as polyethylene glycol and optionally crosslinked. Such polymers are described in particular in French patent 1,222,944 and German patent application 2,330,956, the disclosures of which are specifically incorporated by reference herein. Mention may be made in particular of the copolymers containing an optionally N-alkylated and/or hydroxyalkylated acrylamide unit in their chain as described in particular in Luxembourg patent applications 75370 and 75371, the disclosure of which is specifically incorporated by reference herein, or sold under the name QUADRAMER by the company American Cyanamid. Mention may also be made of copolymers of acrylic acid and of $C_1$–$C_4$ alkyl methacrylate and terpolymers of vinylpyrrolidone, of (meth) acrylic acid and of (meth)acrylate of $C_1$–$C_{20}$ alkyl, for example lauryl (such as the product sold by the company ISP under the name ACRYLIDONE LM), tert-butyl (LUVIFLEX VBM 70 sold by BASF) or methyl (STEPANHOLD EXTRA sold by Stepan) and methacrylic acid/ethyl acrylate/tert-butyl acrylate terpolymers such as the product sold under the name LUVIMER 100 P by the company BASF.

C) Copolymers derived from crotonic acid such as those containing vinyl acetate or propionate units in their chain and optionally other monomers such as allylic esters or methallylic esters, vinyl ether or vinyl ester of a linear or branched saturated carboxylic acid with a long hydrocarbon chain such as those containing at least 5 carbon atoms, it being possible for these polymers optionally to be grafted and crosslinked, or alternatively a vinyl, allylic or methallylic ester of an α- or β-cyclic carboxylic acid. Such polymers are described, inter alia, in French patents 1,222,944, 1,580,545, 2,265,782, 2,265,781, 1,564,110 and 2,439,798, the disclosures of which are specifically incorporated by reference herein. Commercial products falling into this class are the resins 28-29-30, 26-13-14 and 28-13-10 sold by the company National Starch.

D) Copolymers derived from C4–C8 monounsaturated carboxylic acids or anhydrides selected from:
copolymers comprising (i) one or more maleic, fumaric or itaconic acids or anhydrides and (ii) at least one monomer selected from vinyl esters, vinyl ethers, vinyl halides, phenylvinyl derivatives, acrylic acid and its esters, the anhydride functions of these copolymers optionally being monoesterified or monoamidated. Such polymers are described in particular in U.S. Pat. Nos. 2,047,398, 2,723,248 and 2,102,113 and GB patent 839,805, the disclosures of which are specifically incorporated by reference herein, and in particular those sold under the names GANTREZ AN or ES and AVANTAGE CP by the company ISP;

copolymers comprising (i) one or more maleic, citraconic or itaconic anhydrides and (ii) one or more monomers selected from allylic or methallylic esters optionally containing one or more acrylamide, methacrylamide, α-olefin, acrylic or methacrylic ester, acrylic or methacrylic acid or vinylpyrrolidone groups in their chain, the anhydride functions of these copolymers optionally being monoesterified or monoamidated.

These polymers are described, for example, in French patents 2,350,384 and 2,357,241, the disclosures of which are specifically incorporated by reference herein.

E) Polyacrylamides containing carboxylate groups.

The polymers comprising sulphonic groups are polymers containing vinylsulphonic, styrenesulphonic, naphthalenesulphonic or acrylamidoalkylsulphonic units.

These polymers can be selected in particular from:

polyvinylsulphonic acid salts having a weight-average molecular weight ranging from approximately 1000 to approximately 100,000, as well as the copolymers with an unsaturated comonomer such as acrylic or methacrylic acids and their esters, as well as acrylamide or its derivatives, vinyl ethers and vinylpyrrolidone;

polystyrenesulphonic acid salts, the sodium salts having a weight-average molecular weight of about 500,000 and about 100,000, which are sold respectively under the names FLEXAN 500 and FLEXAN 130 by National Starch. These compounds are described in patent FR 2,198,719, the disclosure of which is specifically incorporated by reference herein;

polyacrylamidesulphonic acid salts, those mentioned in U.S. Pat. No. 4,128,631, the disclosure of which is specifically incorporated by reference herein, and more particularly polyacrylamidoethylpropanesulphonic acid sold under the name COSMEDIA POLYMER HSP 1180 by Henkel.

According to the invention the anionic fixing polymers are preferably selected from acrylic acid copolymers such as the acrylic acid/ethyl acrylate/N-tert-butylacrylamide terpolymers sold in particular under the name ULTRAHOLD STRONG by the company BASF, copolymers derived from crotonic acid such as the vinyl acetate/vinyl tert-butylbenzoate/crotonic acid terpolymers and the crotonic acid/vinyl acetate/vinyl neododecanoate terpolymers sold in particular under the name RESIN 28-29-30 by the company National Starch, polymers derived from maleic, fumaric or itaconic acids or anhydrides with vinyl esters, vinyl ethers, vinyl halides, phenylvinyl derivatives or acrylic acid and its esters, such as the methyl vinyl ether/maleic anhydride monoesterified copolymers sold, for example, under the name GANTREZ by the company ISP, the copolymers of methacrylic acid and of methyl methacrylate sold under the name EUDRAGIT L by the company Rohm Pharma, the copolymers of methacrylic acid/methyl methacrylate/$C_1$–$C_4$ alkyl acrylate/acrylic acid or $C_1$–$C_4$ hydroxyalkyl methacrylate which are sold in the form of dispersions under the name AMERHOLD DR 25 by the company Amerchol or under the name ACUDYNE 255 by the company Rohm & Haas, the copolymers of methacrylic acid and of ethyl acrylate sold under the name LUVIMER MAEX or MAE by the company BASF and the vinyl acetate/crotonic acid copolymers and the vinyl acetate/crotonic acid copolymers grafted with polyethylene glycol, sold under the name ARISTOFLEX A by the company BASF.

The anionic fixing polymers which are more particularly preferred are selected from the monoesterified methyl vinyl ether/maleic anhydride copolymers sold under the name GANTREZ ES 425 by the company ISP, the acrylic acid/ethyl acrylate/N-tert-butylacrylamide terpolymers sold under the name ULTRAHOLD STRONG by the company BASF, the copolymers of methacrylic acid and of methyl methacrylate sold under the name EUDRAGIT L by the company Rohm Pharma, the vinyl acetate/vinyl tert-butylbenzoate/crotonic acid terpolymers and the crotonic acid/vinyl acetate/vinyl neododecanoate terpolymers sold under the name RESIN 28-29-30 by the company National Starch, the copolymers of methacrylic acid and of ethyl acrylate sold under the name LUVIMER MAEX or MAE by the company BASF and the vinyl pyrrolidone/acrylic acid/lauryl methacrylate terpolymers sold under the name ACRYLIDONE LM by the company ISP.

The amphoteric fixing polymers which can be used in accordance with the invention can be selected from polymers containing units B and C distributed randomly in the polymer chain, in which B denotes a unit derived from a monomer containing at least one basic nitrogen atom and C denotes a unit derived from an acid monomer containing one or more carboxylic or sulphonic groups, or alternatively B and C can denote groups derived from carboxybetaine or sulphobetaine zwitterionic monomers; B and C can also denote a cationic polymer chain containing primary, secondary, tertiary or quaternary amine groups, in which at least one of the amine groups bears a carboxylic or sulphonic group connected via a hydrocarbon radical or alternatively B and C form part of a chain of a polymer containing an α,β-dicarboxylic ethylene unit in which one of the carboxylic groups has been made to react with a polyamine containing one or more primary or secondary amine groups.

The amphoteric fixing polymers corresponding to the definition given above which are more particularly preferred are selected from the following polymers:

(1) Polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylate and acrylate, dialkylaminoalkylmethacrylamides and -acrylamides. Such compounds are described in U.S. Pat. No. 3,836,537, the disclosure of which is specifically incorporated by reference herein.

(2) Polymers containing units derived from:
a) at least one monomer selected from acrylamides and methacrylamides substituted on the nitrogen with an alkyl radical,
b) at least one acidic comonomer containing one or more reactive carboxylic groups, and
c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides which are more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are selected more particularly from acrylic acid, methacrylic acid, crotonic acid, itaconic acid, maleic acid and fumaric acid and alkyl monoesters, having from 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer such as the products sold under the name AMPHOMER or LOVOCRYL 47 by the company National Starch are particularly used.

(3) crosslinked and alkylated polyamino amides partially or totally derived from polyamino amides of formula (III):

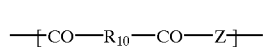

(III)

in which:

$R_{10}$ represents a divalent radical derived from a saturated dicarboxylic acid, a mono- or dicarboxylic aliphatic acid containing an ethylenic double bond, an ester of a lower alkanol, having from 1 to 6 carbon atoms, of these acids or a radical derived from the addition of any one of the acids to a bis(primary) or bis(secondary) amine, and Z denotes a bis(primary), mono- or bis(secondary) polyalkylene-polyamine radical and preferably represents:

a) in proportions of from 60 to 100 mol %, the radical

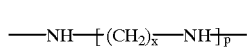

(IV)

where x=2 and p=2 or 3, or alternatively x=3 and p=2 this radical being derived from diethylenetriamine, from triethylenetetraamine or from dipropylenetriamine;

b) in proportions of from 0 to 40 mol %, the radical (IV) above in which x=2 and p=1 and which is derived from ethylenediamine, or the radical derived from piperazine:

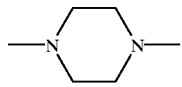

c) in proportions of from 0 to 20 mol %, the —NH—(CH$_2$)$_6$—NH— radical derived from hexamethylenediamine, these polyamino amines being crosslinked by addition of a difunctional crosslinking agent selected from epihalohydrines, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably selected from acids having from 6 to 10 carbon atoms, such as adipic acid, 2,2,4-trimethyladipic acid and 2,4,4-trimethyladipic acid, terephthalic acid, acids containing an ethylenic double bond such as, for example, acrylic acid, methacrylic acid and itaconic acid.

The alkane sultones used in the alkylation are preferably propane sultone or butane sultone, the salts of the alkylating agents are preferably the sodium or potassium salts.

(4) polymers containing zwitterionic units of formula (V):

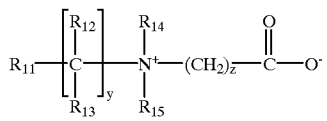

(V)

in which:

$R_{11}$ denotes a polymerizable unsaturated group such as an acrylate, methacrylate, acrylamide or methacrylamide group, y and z represent an integer ranging from 1 to 3, $R_{12}$ and $R_{13}$ represent a hydrogen atom, methyl, ethyl or propyl, $R_{14}$ and $R_{15}$ represent a hydrogen atom or an alkyl radical such that the sum of the carbon atoms in $R_{14}$ and $R_{15}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of methyl methacrylate/dimethyl carboxymethylammonio methyl ethylmethacrylate such as the product sold under the name DIAFORMER Z301 by the company Sandoz.

(5) Polymers derived from chitosan containing monomer units corresponding to the following formulae:

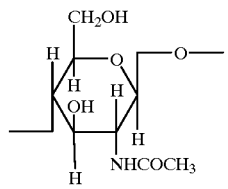

(D)

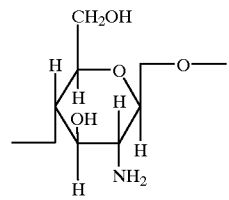

(E)

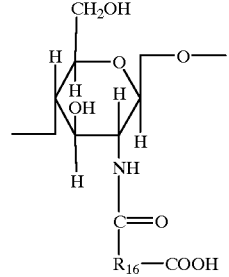

(F)

the unit D being present in a concentration ranging from 0 to 30%, the unit E in a concentration ranging from 5 to 50%, and the unit F in a concentration ranging from 30 to 90%, it being understood that, in this unit F, $R_{16}$ represents a radical of formula:

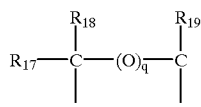

in which, if q=0, $R_{17}$, $R_{18}$ and $R_{19}$ each independently represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulphonic groups, an alkylthio residue in which the alkyl group bears an amino residue, at least one of the radicals $R_{17}$, $R_{18}$ and $R_{19}$ being, in this case, a hydrogen atom;

or, if q=1, $R_{17}$, $R_{18}$ and $R_{19}$ each independently represent a hydrogen atom, as well as the salts formed by these compounds with bases or acids.

(6) Polymers derived from the N-carboxyalkylation of chitosan, such as N-carboxymethylchitosan or N-carboxybutylchitosan sold under the name "EVALSAN" by the company Jan Dekker.

(7) Polymers corresponding to the formula (VI) are described, for example, in French patent 1,400,366, the disclosure of which is specifically incorporated by reference herein:

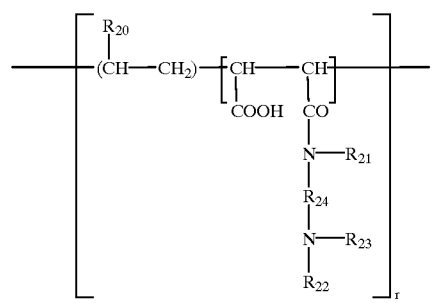

(VI)

in which:

$R_{20}$ represents a hydrogen atom, a $CH_3O$, $CH_3CH_2O$ or phenyl radical, $R_{21}$ denotes hydrogen or a lower alkyl radical such as methyl or ethyl, $R_{22}$ denotes hydrogen or a lower alkyl radical such as methyl or ethyl, $R_{23}$ denotes a lower alkyl radical such as methyl or ethyl or a radical corresponding to the formula: $-R_{24}-N(R_{22})_2$, wherein $R_{22}$ can be the same or different, $R_{24}$ representing a $-CH_2-CH_2-$, $-CH_2-CH_2-CH_2-$ or $-CH_2-CH(CH_3)-$ group, and the higher homologues of these radicals containing up to 6 carbon atoms.

(8) Amphoteric polymers of the type $-D-X-D-X$ selected from:

a) polymers obtained by the action of chloroacetic acid or sodium chloroacetate on compounds containing at least one unit of formula:

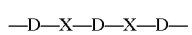 (VII)

where D denotes a radical

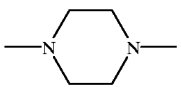

and X denotes the symbol E or E', E or E', which may be identical or different, denotes a divalent radical which is an alkylene radical containing a straight or branched chain containing up to 7 carbon atoms in the main chain, which is unsubstituted or substituted with hydroxyl groups and which can contain, in addition to the oxygen, nitrogen and sulphur atoms, from 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups.

b) Polymers of formula:

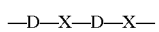 (VII')

in which D denotes a radical

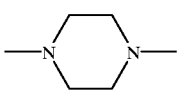

and X denotes the symbol E or E' and at least once E', E having the meaning given above and E' is a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) ($C_1$–$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

The amphoteric fixing polymers which are particularly preferred according to the invention are those of family (3), such as the copolymers whose CTFA name is octylacrylamide/acrylates/butylaminoethyl methacrylate copolymer, such as the products sold under the names AMPHOMER, AMPHOMER LV 71 or LOVOCRYL 47 by the company National Starch and those of family (4) such as the copolymer of methyl methacrylate/dimethyl carboxymethylammonio methyl ethylmethacrylate, sold, for example, under the name DIAFORMER Z301 by the company Sandoz.

The anionic or amphoteric fixing polymers can, if necessary, be partially or totally neutralized. The neutralizing agents are, for example, sodium hydroxide, potassium hydroxide, 2-amino-2-methyl-1-propanol, monoethanolamine, triethanolamine or triisopropanolamine and inorganic or organic acids such as hydrochloric acid or citric acid.

Advantageously, the appropriate solvent contains at least 50% by volume of alcohol, preferably at least 70% by volume of alcohol. According to the invention, the term alcohol is understood to refer to a $C_1$–$C_4$ aliphatic alcohol, preferably ethanol.

The propellant comprises the compressed or liquefied gases usually used for the preparation of aerosol compositions. Air, carbon dioxide or nitrogen, which are compressed, or alternatively a gas which may or may not be soluble in the composition, such as dimethyl ether, hydrocarbons and mixtures thereof, will preferably be used.

Depending on the aerosol composition (fluid+propellant), a person skilled in the art will know how to select the appropriate distribution means in order to obtain the desired solids flow rate and wetting power characteristics.

The specific characteristics defined above ($C_S$ and phase) can be obtained by selecting the appropriate distribution means and/or by varying the formulation.

The appropriate valves for the specific compositions above are, in particular, straight valves with a nozzle having a diameter ranging from 0.35 to 0.60 mm, preferably from 0.40 to 0.50 mm, advantageously with no internal restriction or any additional uptake of gas. These are, in particular, the valves sold under the name COSTER T104 RA36/0/4 by the company Coster or the valve PRECISION EXPERIMENTAL 15130, comprising a nozzle and a valve body 0.46 mm in diameter with no additional gas uptake, from the company Precision.

The appropriate diffusers for the specific compositions above are, in particular, the push-button dispensers sold under the name PRECISION 216903-40AD29 by the company Precision.

The present invention also relates to a process for treating keratin fibers, in which a composition comprising a fixing material having a glass transition temperature (Tg) of greater than or equal to 30° C. is applied to the fibers by means of an appropriate device in order to obtain a solids flow rate ranging from approximately 4 to approximately 17 mg/s and a wetting power of greater than or equal to 50 mg/s.

The examples below allow the invention to be illustrated without, however, limiting its scope.

Example 1

Importance of the "Wetting Power" for Lacquering

The two aerosol devices below were prepared:
Device 1 (According to the Invention)
The following fluid was prepared:
Composition A

| | |
|---|---|
| Acrylic acid/ethyl acrylate/N-tert-butylacrylamide terpolymer sold under the name ULTRAHOLD STRONG by the company BASF | 3.10 g |
| 2-Amino-2-methyl-1-propanol Neutralization | q.s. |
| Ethanol | q.s. 100.00 g |

65 g of this fluid were introduced into an aerosol can which was then fitted with a PRECISION EXPERIMENTAL 15130 valve, after which 35 g of dimethyl ether were added as propellant and a PRECISION 216903-40AD29 bush-button dispenser.

The characteristics of this device were as follows:

| | | |
|---|---|---|
| Tg of the fixing material | : | 51° C. |
| $F_S$ | : | 11 mg/s |

| | | |
|---|---|---|
| Wetting power | : | 55 mg/s |
| $F_{AC}$ | : | 550 mg/s |

Device 2 (Comparative)
The following fluid was prepared:
Composition B

| | |
|---|---|
| Acrylic acid/ethyl acrylate/N-tert-butylacrylamide terpolymer sold under the name ULTRAHOLD STRONG by the company BASF | 4.28 g |
| 2-Amino-2-methyl-1-propanol Neutralization | q.s. |
| Ethanol | q.s. 100.00 g |

35 g of this fluid and 20 g of pentane were introduced into an aerosol can which was fitted with a PRECISION P155/590 valve (sold by the company Precision), after which 43 g of dimethyl ether were added as propellant, and a PRECISION 21 6943-40 push-button dispenser (sold by the company Precision).

The characteristics of this device were as follows:

| | | |
|---|---|---|
| Tg of the fixing material | : | 51° C. |
| $F_S$ | : | 11 mg/s |
| Wetting power | : | 10 mg/s |
| $F_{AC}$ | : | 700 mg/s |

These two devices were tested on heads (20 s per head). The tests showed that only the device according to the invention allowed a desired cosmetic fixing effect to be obtained. In contrast, device 2 (comparative) did not allow a satisfactory cosmetic fixing result to be obtained.

Example 2

Importance of the "Tg" for Obtaining Good Cosmetic Properties

The following fluids were prepared:
Composition C

| | |
|---|---|
| VA/vinyl butylbenzoate/crotonates copolymer (CTFA) | 4.28 g |
| 2-Amino-2-methyl-1-propanol Neutralization | q.s. |
| Tripropylene glycol monomethyl ether | 0.29 g |
| Ethanol | q.s. 100.00 g |

Composition D

| | |
|---|---|
| VA/vinyl butylbenzoate/crotonates copolymer (CTFA) | 4.28 g |
| 2-Amino-2-methyl-1-propanol Neutralization | q.s. |
| Ethanol | q.s. 100.00 g |

The aerosol devices 3 and 4 were prepared by introducing 65 g of compositions C and D respectively into aerosol cans. The two cans were fitted with a PRECISION EXPERIMENTAL 15130 valve and 35 g of dimethyl ether as propellant, and a PRECISION 216903-40AD29 push-button dispenser were then added.

For the two devices, the $F_S$ was 14.3 mg/s and the wetting power was 62 mg/s.

The Tg values of the fixing materials in the two devices were as follows:

| | | |
|---|---|---|
| Tg device 3 (comparative) | : | 23° C. |
| Tg device 4 (according to the invention) | : | 41° C. |

The performance levels of the two devices were compared by spraying the two compositions on 10 heads in half-head tests. In all cases, the fixing powers were satisfactory and comparable. On the other hand, the side treated with device 4 according to the invention felt more pleasant than the side treated with comparative device 3, and likewise the disentangling was easier on the side treated with device 4 according to the invention, and the feel after disentangling was also considered to be more pleasant.

Example 3

Importance of the "$F_S$" for Obtaining Good Cosmetic Properties

The following two fluids were prepared:

Composition E

| | |
|---|---|
| VA/vinyl butylbenzoate/crotonates copolymer (CTFA) | 4.00 g |
| 2-Amino-2-methyl-1-propanol | q.s. |
| Neutralization | |
| Ethanol | q.s. 100.00 g |

Composition F

| | |
|---|---|
| VA/vinyl butylbenzoate/crotonates copolymer (CTFA) | 5.00 g |
| 2-Amino-2-methyl-1-propanol | q.s. |
| Neutralization | |
| Ethanol | q.s. 100.00 g |

Aerosol devices 5 and 6 were prepared by introducing 65 g of compositions E and F respectively into aerosol cans. The two cans were fitted with a PRECISION EXPERIMENTAL 15130 valve and 35 g of dimethyl ether as propellant, and a PRECISION 216903-40AD29 push-button dispenser were then added.

For the two devices, the Tg of the fixing material was 41° C. and the wetting power was 62 mg/s.

The $F_S$ values of the fixing materials in the two devices were as follows:

| | |
|---|---|
| $F_S$ device 5 (according to the invention) | : 15.0 mg/s |
| $F_S$ device 6 (comparative) | : 18.5 mg/s |

The performance levels of the two devices were compared by spraying the two compositions on 10 heads in half-head tests. In all cases, the fixing powers were satisfactory and comparable. On the other hand, the side treated with device 5 according to the invention felt more pleasant than the side treated with comparative device 6, and likewise the disentangling was easier on the side treated with device 5 according to the invention, and the feel after disentangling was also considered to be more pleasant.

Example 4

Comparisons

The disentangling properties obtained with device 4 (65 g of composition D, PRECISION EXPERIMENTAL valve 15130, 35 g of dimethyl ether, PRECISION 216903-40AD29 push-button dispenser) were compared with those of commercial devices.

| Device | Tg | $F_S$ | Wetting power | Disentangling |
|---|---|---|---|---|
| Device 4 | 41° C. | 14.3 mg/s | 62 mg/s | +++ |
| *Pantene Pro V ® | 50° C. | 17.4 mg/s | >190 mg/s | ++ |
| **Aqua Net ® | 23° C. | 16.8 mg/s | 190 mg/s | + |
| ***Elnett ® Fixation Forte | <30° C. | >20 mg/s | 40 mg/s | ++ |

*Sold by Procter & Gamble
**Sold by Faberge
***Sold by L'Oreal
+ to +++ represent an increasing scale of the disentangling qualities of the various compositions.

The results of the above table are in accordance with those results observed in Examples 1 to 3, in which only the device satisfying the three characteristics of "Tg", "$F_S$" and "wetting power" according to the invention allows both strong fixing and improved cosmetic properties to be obtained.

We claim:

1. An aerosol device, comprising:
   a container containing an aerosol composition, said composition comprising a liquid phase containing at least one fixing material in a suitable solvent and a propellant, wherein said at least one fixing material has a glass transition temperature (Tg) of greater than or equal to 30° C.; and
   a means for distributing said aerosol composition, wherein said aerosol device is suitable for obtaining a solids flow rate for said aerosol composition ranging from approximately 4 to approximately 17 mg/s and a wetting power for said aerosol composition of greater than or equal to 50 mg/s.

2. An aerosol device according to claim 1, wherein said aerosol device is suitable for obtaining a solids flow rate of less than 16 mg/s.

3. An aerosol device according to claim 2, wherein said aerosol device is suitable for obtaining a solids flow rate ranging from 6 to 15 mg/s.

4. An aerosol device according to claim 1, wherein said aerosol device is suitable for obtaining a wetting power ranging from 50 mg/s to 125 mg/s.

5. An aerosol device according to claim 1, wherein said aerosol composition has a solids concentration ($C_S$) ranging from 0.4 to 5% by weight relative to the total weight of said aerosol composition.

6. An aerosol device according to claim 5, wherein said solids concentration ranges from 0.6 to 3.25% by weight relative to the total weight of said aerosol composition.

7. An aerosol device according to claim 1, wherein said aerosol composition has a flow rate ($F_{AC}$) ranging from approximately 500 to approximately 700 mg/s.

8. An aerosol device according to claim 7, wherein said flow rate is approximately 550 mg/s.

9. An aerosol device according to claim 1, wherein said aerosol composition has a fluid/propellant weight ratio of greater than 1.

10. An aerosol device according to claim 9, wherein said fluid/propellant weight ratio ranges from 1.2 to 3.

11. An aerosol device according to claim 1, wherein said at least one fixing material comprises at least one fixing polymer.

12. An aerosol device according to claim 11, wherein said at least one fixing polymer is an anionic, cationic, amphoteric or nonionic polymer.

13. An aerosol device according to claim 12, wherein said at least one fixing polymer is an anionic or amphoteric polymer.

14. An aerosol device according to claim 1, wherein said suitable solvent contains at least 50% by volume of alcohol.

15. An aerosol device according to claim 14, wherein said suitable solvent contains at least 70% by volume of alcohol.

16. A process for treating a keratin fiber comprising applying to said keratin fiber a composition comprising at least one fixing material having a glass transition temperature (Tg) of greater than or equal to 30° C., said applying being accomplished by a suitable device capable of obtaining a solids flow rate for said composition ranging from approximately 4 to approximately 17 mg/s and a wetting power for said composition of greater than or equal to 50 mg/s.

17. An aerosol device, comprising:

a container containing an aerosol composition, said composition comprising a liquid phase containing at least one fixing material in a suitable solvent and a propellant, wherein said at least one fixing material has a glass transition temperature (Tg) of greater than or equal to 30° C.; and a distribution valve controlled by a distribution head comprising a nozzle through which said aerosol composition is distributed, wherein said aerosol device is suitable for obtaining a solids flow rate for said aerosol composition ranging from approximately 4 to approximately 17 mg/s and a wetting power for said aerosol composition of greater than or equal to 50 mg/s.

18. A process for treating a keratin fiber comprising:

applying to said keratin fiber a composition at a solids flow rate ranging from 4 to 17 mg/s and at a wetting power greater than or equal to 50 mg/s, wherein said composition comprises at least one fixing material having a glass transition temperature (Tg) of greater than or equal to 30° C.

* * * * *